United States Patent [19]

Hargrave

[11] 4,156,118
[45] May 22, 1979

[54] AUDIOMETRIC HEADSET

[76] Inventor: Frances E. Hargrave, 5739 Camellia Ave., Temple City, Calif. 91780

[21] Appl. No.: 894,659

[22] Filed: Apr. 10, 1978

[51] Int. Cl.² .............................................. H04R 1/10
[52] U.S. Cl. ................................................ 179/182 R
[58] Field of Search ................................... 179/182 R

[56] References Cited

U.S. PATENT DOCUMENTS 3,220,505  11/1965  Hargrave ..................... 179/182 R X Primary Examiner—William C. Cooper
Attorney, Agent, or Firm—Jessup & Beecher

[57] ABSTRACT

An audiometric headset having a transducer mounting and sound insulation system which closely couples the transducer to the ear. The headset is comprised of a pair of domes having a soft foam liner and soft sponge sound-absorbent material surrounding a floating sound transducer mounted in an open side of the case. The sound transducer is mounted in a socket of a circular resilient hub supported on a resilient flange by a pair of resilient strips providing a semi-circular opening between the interior of the case and the exterior of the earpiece. The resilient flange provides a channel for mounting on a rim around the periphery of the opening in the dome or case. An ear cushion snap-locked into a channel surrounding the socket supporting the transducer closely couples the transducer to the ear. A resilient earmuff is mounted around the rim of the case opening and is filled with a sound-filtering soft material whereby the muff seals around the ear to eliminate external ambient noise.

5 Claims, 4 Drawing Figures

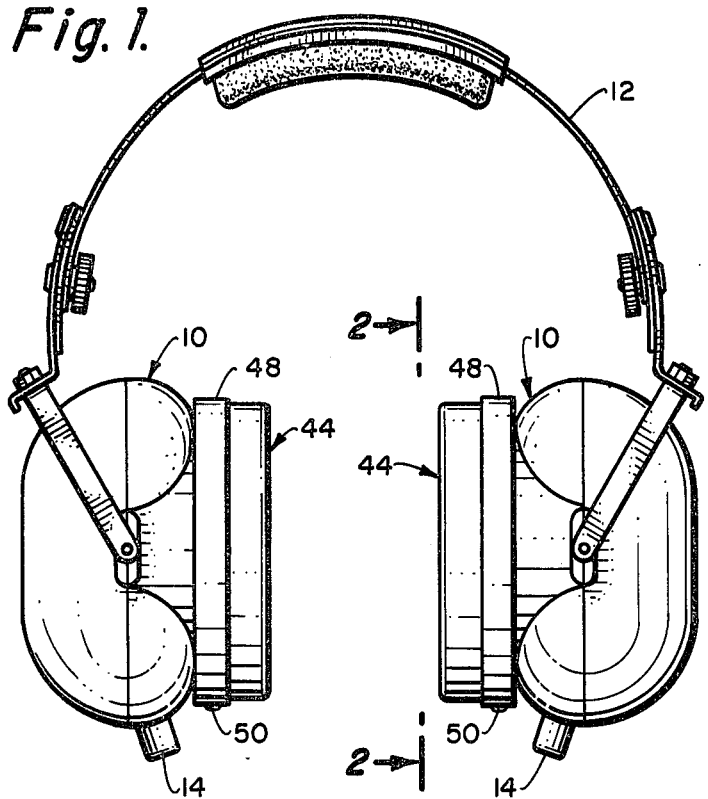
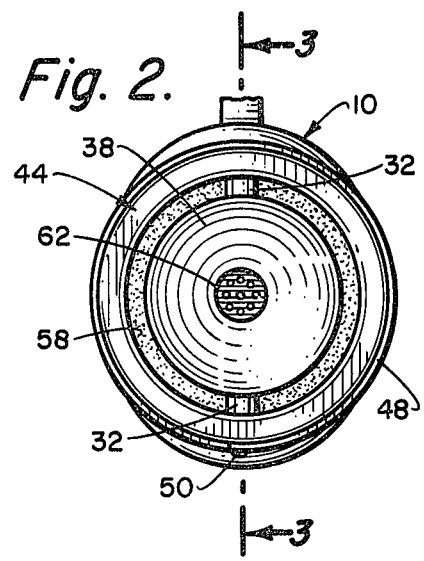
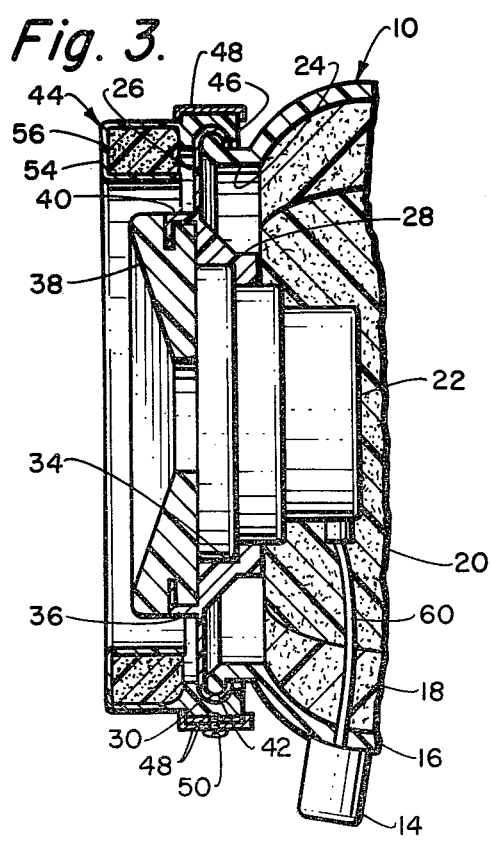
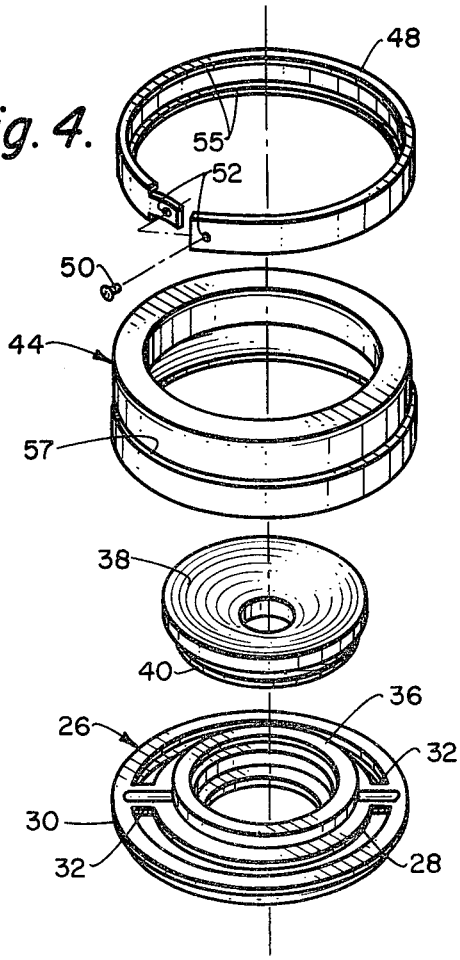

AUDIOMETRIC HEADSET

BACKGROUND OF THE INVENTION

This invention relates generally to audiometric headsets and particularly to a headset for making tests in the presence of ambient noise.

In making hearing tests it is essential that the signals arriving at the ear drum be closely coupled and controlled. Thus, in making such tests, sound-proof booths are frequently utilized. The use of such booths greatly adds to the expense involved in setting up test facilities, as well as reducing the number of patients which can be tested by requiring a great deal of space.

Headsets have been constructed to substantially eliminate outside influences or noises and one such headset is shown in U.S. Pat. No. 3,220,505, issued Nov. 30, 1965. While this headset has been an improvement, it has not been entirely satisfactory in providing the adaptability or ease of removal, replacement and maintenance of parts desired. It would be desirable if individual parts of the device could be readily removed and replaced, repaired and maintained while still providing close coupling, sound insulation and isolation of the speaker or transducer.

SUMMARY OF THE INVENTION

The purpose of the present invention is to provide an audiometric headset which provides an independent floating mount for a sound transducer or speaker to prevent vibrations and a resilient mounting to seal against outside noises.

An audiometric headset is disclosed in which a pair of domes or cases are provided having an opening on one side. The domes or cases are filled with a sound-filtering liner covering substantially the entire inside surface of the dome with the remaining area being filled with a soft, sound-absorbing foam surrounding the sound transducer. The sound transducer or speaker is mounted in the opening in the dome by a resilient hub having a socket fitted around the transducer. The hub is supported by strips, spokes or webs substantially isolating the transducer from the dome, preventing any mechanical transference of vibrations. The strips supporting the hub are connected to a flange forming a channel which snaps around a peripheral rim on the opening of the housing.

A resilient ear cushion is fitted onto the hub to secure the transducer in the hub socket and provide coupling of the transducer to the ear when the headset is being worn. The ear cushion has a peripheral flange or lip which snaps into a peripheral channel around the socket opening for the transducer which allows the ear cushion and the transducer to be easily removed and calibrated, repaired, cleaned or replaced. The hub is secured to the flange by only two strips or spokes, permitting considerable adjustment of the ear cushion on the ear of the wearer. This allows the transducer mounting system of the hub and ear cushion considerable flexibility to adjust for the particular wearer. In addition, this type of support minimizes the amount of material connecting the transducer to the case, thus eliminating substantially all possibility of any mechanical vibrations being transmitted from the dome to the transducer or vice versa.

A resilient earmuff seal is mounted around the rim of the opening in the case to press against the side of the head, substantially sealing the ear from any outside ambient noises. The resilient earmuff seal has a flange which fits over the flange supporting the hub, both of which are held in place by a circular metal band fastened by a screw, which may be easily removed. The earmuff seal is formed with a flexible skirt forming a circular cavity filled with a soft, foam, sound-absorbing filtering material. Thus, a construction is provided in which all the respective resilient parts may be easily removed, inspected, repaired, replaced or cleaned, if desired. The headset thus is adapted for accurate hearing measurements while being easily assembled and disassembled without the use of any special tools.

It is therefore an object of this invention to provide an improved audiometric headset.

It is a further object of the present invention to provide an improved mounting for the sound transducer which isolates the sound transducer from vibrations.

Yet another object of the present invention is to provide an audiometric headset which substantially minimizes the influence of outside noises.

Still another object of the present invention is the provision of an audiometric headset which can have the individual parts forming the ear coupling function easily removed for maintenance, replacement and calibration.

Other objects, advantages and novel features of the invention become apparent from the following detailed description of the invention when considered in conjunction with the accompanying drawings, wherein like reference numbers identify like parts throughout.

BRIEF DESCRIPTION OF THE DRAWINGS

FIG. 1 is a view of the audiometric headset according to the invention.

FIG. 2 is a view of one of the ear coupling assemblies taken at 2—2 of FIG. 1.

FIG. 3 is a sectional view through the ear assembly of FIG. 2 taken at 3—3.

FIG. 4 is an exploded view of the transducer mounting and ear coupling assembly according to the invention.

DETAILED DESCRIPTION OF THE PREFERRED EMBODIMENT

Referring to FIG. 1, there is shown an audiometric headset comprised of earphones 10 adjustably mounted on a head band 12. Each earphone 10 is identically constructed as illustrated in FIGS. 2 through 4. Electrical connections to the earphones 10 are provided through connectors 14 at the bottom of each earphone.

Each earphone 10 has an assembly as illustrated in FIG. 3 for coupling sound reproduction to the ear. The earphone 10 is constructed of a case 16 having a soft liner 18 substantially as illustrated in U.S. Pat. No. 3,220,505. The remaining portion of the case is filled with a soft sound-absorbent foam 20 surrounding a sound transducer 22 mounted in the opening 24 in the case 16.

In order to isolate the sound transducer 22 from the case 16, a transducer mounting trunnion diaphragm 26 is provided, having a hub 28 secured to a flange 30 by strips, spokes or webs 32. The hub 28 has a socket 34 for receiving of the transducer 22. In order to secure the transducer 22 in socket 34, a flange 36 is provided around the socket 34 into which an ear cushion 38 fits by means of a mating flange 40. The flange 30 of the transducer mounting trunnion diaphragm 26 snaps around a rounded lip or rim 42 on the periphery of the opening 24 in the dome or case 16. This transducer mounting trunnion diaphragm 26 thus provides a free-floating or independent mounting for the transducer 22 isolating it from the dome or case 16 to minimize any possible transfer of mechanical vibrations. The only connection between the transducer mounting system and the outer case 16 is the soft sound-absorbing foam 20 and the webbing 32 supporting the hub 36.

As can be seen, the ear cone or cushion 38 may be easily removed for calibration, maintenance and repair of the cone or sound transducer 22.

For comfort and to seal off outside or ambient noises, an earmuff seal 44 is provided. Earmuff seal 44 also has a flange 46 fitting over the flange 30 around the rim or lip 42 on the case opening 24. The flanges 46 and 30 of the earmuff and diaphragm respectively, are clamped securely on the lip 42 by means of a ring 48 which is secured by a screw 50. The ring or flange 48 is placed around the flange 46 of the earmuff seal 44 and squeezed slightly to permit insertion of screw 50 in holes 52, in the metal band or ring 48. The ring 48 is retained securely on flange 46 by a raised ridge 57 engaging a lip 55 on the ring. Thus, the ring or band 48 securely clamps the flanges on the peripheral rim 42 of the case 16. To remove any or all of the assembly, the ring or band 48 can be squeezed slightly and the screw 50 easily withdrawn from overlapping holes 52. This will permit removal and replacement of any or all of the parts functioning to couple the transducer 22 to the ear of the wearer.

The earmuff seal 44 is formed with a flexible skirt 54 providing an annular cavity filled with a sound filter 56 which provides added comfort and support on the wearer and also provides additional insulation from ambient or outside noises.

Thus, the transducer 22 is supported by the diaphragm 26 in a free-floating completely independent or isolated manner from the case 16. The use of just two strips or spokes or flexible connections for the hub 28 to the flange 30 provides maximum isolation of the transducer 22, while also permitting great flexibility of the ear cushion 38 on the ear of the wearer. As can be seen in FIG. 2, the flanges 32 connecting the hub 28 to the flange 30 provide semi-circular apertures 58 around the transducer to acoustically couple the interior of the dome with the chamber formed by flexible skirt 54 to prevent resonance and distortion.

When used, the earphones 10 are placed on the ears of the user with the earmuff seal 44 substantially surrounding and covering the ear with the ear cushion 38 being pressed against the ear of the user. The flexible mounting provided by the strips or spokes 32 for the transducer assembly allows considerable adjustment of the ear cushion 38 on the user. Electrical sound signals are conveyed to the speaker 22 by means of wire leads 60 leading to terminals 14 on the case 16. The headset is adapted for use with standard audiometers without changing calibration of the earphone output, and provides a simple yet highly efficient means for enabling accurate audiometric tests under conditions of ambient noise. The ear cushion or cone 38 couples the sound from this speaker or transducer 22 by cooperating with the auricle portion of an average human ear to form a sound pressure chamber therewith. The ear cushion 38 has a central aperture or opening 62 coupling the sound from the transducer to the auricle portion of the human ear.

In addition to providing an ear coupling assembly which can be easily removed and replaced, the transducer mounting trunnion diaphragm 26 provides great flexibility and isolation for the speaker or transducer 22. The accurate calibration and fitting of the headphones to all ears requires not only resiliency but an ability to tip for adaptation to various ear structures while still providing the necessary independence and isolation. The novel and unique ear coupling assembly described herein provides both of these functions very efficiently.

Thus, there has been disclosed a new earphone assembly providing an ear coupling assembly which can be easily removed for calibration, replacement and repair. In addition, the ear coupling assembly provides a mounting for the speaker or sound transducer which completely isolates the transducer from any mechanical vibrations.

Obviously, many modifications and variations of the present invention are possible in light of the above teachings. It is therefore to be understood that the full scope of the invention is not limited to the details disclosed herein but may be practiced otherwise than as specifically described.

What is claimed is:

1. An audiometric headset comprising:
 a case having an open end;
 a resilient sound-proofing material in said case;
 a sound transducer;
 mounting means mounting said transducer in the opening in said case;
 said mounting means comprising:
 resilient means having a flange with a channel engaging a peripheral rim of the opening in said case,
 a hub having a socket for supporting said transducer,
 spoke means attaching said hub to said resilient means,
 a resilient ear cushion attached to said hub securing said transducer in said socket,
 a resilient ear seal ring mounted on the rim of said case opening; and
 clamping means clamping said ear seal ring and said resilient means on said rim.

2. The audiometric headset according to claim 1 wherein:
 said ear cushion is removably secured to said hub whereby said ear cushion may be easily removed for repair or replacement of the transducer or cushion.

3. The audiometric headset according to claim 2 wherein:
 said hub has a flange forming a channel around the transducer socket; and
 said ear cushion has a flange fitting said channel whereby said cushion is secured to said hub by a snap lock of said cushion flange into said channel.

4. The audiometric headset according to claim 1 wherein:
 said resilient ear seal has a flexible skirt forming an annular cavity; and
 a resilient foam sound filtering means filling said cavity.

5. The audiometric headset according to claim 1 wherein:
 said spoke means comprises a pair of elastic members flexibly supporting said hub and thereby forming a pair of semi-circular openings around said hub communicating with the interior of said cone;
 whereby said transducer is supported in a substantially free-floating independence from said case.

* * * * *